United States Patent [19]
Dudley

[11] Patent Number: 5,744,731
[45] Date of Patent: *Apr. 28, 1998

[54] LIQUID SAMPLING APPARATUS CAPABLE OF ASSEMBLY IN DIFFERENT SAMPLING CONFIGURATIONS

[75] Inventor: Lynn A. Dudley, Chino, Calif.

[73] Assignee: Vortox Company, Claremont, Calif.

[ * ] Notice: The term of this patent shall not extend beyond the expiration date of Pat. No. 5,524,495.

[21] Appl. No.: 589,719

[22] Filed: Jan. 22, 1996

[51] Int. Cl.⁶ ........................................ G01N 1/12
[52] U.S. Cl. .................. 73/864.63; 73/864.51; 73/864.91; 73/863.52
[58] Field of Search .............. 73/864.63, 864.51, 73/863.52, 863.57, 864.91, 863.53, 170.17–170.23

[56] References Cited

U.S. PATENT DOCUMENTS

| | | | |
|---|---|---|---|
| 2,660,063 | 11/1953 | Sawers | 73/864.51 |
| 3,826,144 | 7/1974 | Wessels | |
| 3,929,003 | 12/1975 | LLewellyn | |
| 4,271,704 | 6/1981 | Peters | |
| 4,718,288 | 1/1988 | Leschonski et al. | 73/863.52 |
| 4,762,009 | 8/1988 | Scrudto | |
| 4,769,215 | 9/1988 | Ehrenkranz | 73/863.52 |
| 4,899,601 | 2/1990 | Lee | 73/864.63 |
| 4,958,528 | 9/1990 | Garrison | |
| 5,069,878 | 12/1991 | Ehrenkranz | |
| 5,186,052 | 2/1993 | Gray | |
| 5,220,825 | 6/1993 | Peterson et al. | |
| 5,279,151 | 1/1994 | Coody et al. | |
| 5,339,676 | 8/1994 | Johnson | 73/863.52 |
| 5,347,877 | 9/1994 | Gadbois | |
| 5,408,892 | 4/1995 | Kawanami et al. | |
| 5,524,495 | 6/1996 | Dudley | 73/864.63 |
| 5,567,889 | 10/1996 | Sullivan et al. | 73/863.52 |

FOREIGN PATENT DOCUMENTS

| 2236522 | 4/1991 | United Kingdom | 73/864.63 |
|---|---|---|---|

OTHER PUBLICATIONS

Water Resources Research publication, article "Development of a Self–Sealing Rain Sampler for Arid Zones", by E. Adar et al, pp. 592–596, vol. 16, No. 3, Jun. 1980.

Levin et al., "Development of a Self–Sealing Sampler for Ephemeral Wadi Floods", 2/1980, pp. 245–250.

*Primary Examiner*—Hezron E. Williams
*Assistant Examiner*—Nashmiya N. Ashraf
*Attorney, Agent, or Firm*—Boniard I. Brown

[57] ABSTRACT

Liquid sampling apparatus includes four components, including a cover, a small receptacle preferably in the form of a glass jar, and intermediate and large receptacles preferably in the form of stainless steel canisters which may be assembled in various combinations to form a variety of liquid sampler configurations or sampling devices.

20 Claims, 5 Drawing Sheets

LIQUID SAMPLING APPARATUS CAPABLE OF ASSEMBLY IN DIFFERENT SAMPLING CONFIGURATIONS

RELATED APPLICATIONS

Reference is made to my applications Ser. No. 08/421,474 now U.S. Pat. No. 5,524,495.

BACKGROUND OF THE INVENTION

1. Field of the Invention

This invention relates generally to the art of sampling liquids for analysis and more particularly to a novel liquid sampling apparatus for sampling storm water runoff from industrial property and other liquids.

2. Discussion of the Prior Art

As will become readily evident from the ensuing description, the liquid sampling apparatus of this invention may be utilized for a variety of liquid sampling purposes and to sample a variety of liquids in various liquid sampling environments. One liquid sampling application of particular importance at the present time involves sampling storm water runoff from a land area, such as an industrial property to determine the presence of toxins and/or other contaminants in the runoff. Another possible sampling application involves sampling liquid leakage from industrial processing equipment to aid in locating the source of the leakage. Other possible sampling applications involve sampling liquid discharge from a sewage treatment plant or an industrial process, and sampling liquid in a body of liquid.

At the present time, there is a particular need to sample storm water runoff from certain areas, particularly industrial properties. In this regard, it is well known that the water flowing through public storm drain systems contain toxins and other contaminants which end up polluting large public water bodies, such as the San Diego, Santa Monica, and San Francisco bays in California. Much of this contamination is due to deliberate dumping of industrial waste products into the storm drain system in order to avoid the problems and costs associated with legal deposition of such waste products. Most of this deliberate dumping occurs in remote areas and/or in the dead of night and is thus very difficult if not impossible to trace back to the original source of the contaminants.

Another extensive source of contamination in the waters of public storm drain systems is storm water runoff from industrial property and the like. The ground, driveways, exterior storage area and other exterior surfaces of such property are often covered by or contain a relatively high concentration of various industrial substances due to spillage of such substances onto these surfaces, leakage of the substances into the soil from pipes or storage containers, and hosing of the substances from interior floor areas onto exterior surface areas and the ground. During a rainstorm, these substances are entrained in the storm water runoff from the property and are carried with the storm water runoff into the public storm drain system.

In an effort to reduce such storm water runoff pollution, the state of California recently passed legislation establishing a program entitled the Industrial Storm Water Permitting Program. This program requires industrial property owners to obtain a permit, referred to as a General Industrial Storm Water Permit, for storm water runoff of discharge from their properties into the public storm drain system. These permits are issued through the State Water Resources Control Board.

Obtaining such a permit involves the payment of an annual fee and the performance by each applicant, referred to as a discharger, of certain obligations. These obligations include the following: (a) preparation of a site map of the property in question, starting with the roof of each building on the property, showing the flow path of storm water runoff from the roof to the ground, then across the ground into the drain system on the property, and then from the property drain system into the public storm drain system; (b) visual observation of storm water discharge from the property during both the wet season (October through April) and the dry season (May through September); (c) submission of an estimate or calculation of the storm water discharge volume during two significant storm events in the wet season; (d) submission, for approval, of a proposed storm water sampling program; (e) execution of the approved storm water sampling program in compliance with the state regulations to obtain certain storm water samples; and (f) submission of the storm water samples for analysis.

Requirement (e) above of the Industrial Storm Water Permitting Program dictates that storm water samples be obtained during two separate storm events of the wet season and that one of these events be the first storm event of the wet season which produces significant storm water runoff preceded by at least 72 hours of dry weather. The storm water samples collected during each storm event must include a "grab sample" and possibly a "composite" sample. A grab sample is a storm water sample taken during the first thirty minutes of the discharge (or within the first hour of the discharge with explanation). A composite sample may be a sample taken with a continuous flow sampler or the combination of at least three grab samples taken during each hour of discharge with the successive being separated by a minimum period of at least 15 minutes. A composite sample shall be flow-weighted (i.e. consist of a mixture of aliquots collected at constant time intervals, where the volume of each aliquot is proportional to the flow rate of the discharge) or time-weighted (i.e. consist of a mixture of equal volume aliquots collected at constant time intervals). Grab samples are used for determining certain specific contamination levels. Composite samples are used to obtain an estimate of average runoff water quality.

From the above discussion, it is evident that storm water sampling in compliance with the above-stated requirements of the Industrial Storm Water Permitting Program presents two basic problems. These problems are: (a) having a storm water sampler in proper sampling readiness and position at the start of the first significant storm event of a wet season to collect a sample of the storm water runoff during the first 30 minutes of the discharge which will qualify as a valid "grab sample", and (b) having a storm water sampler in proper sampling readiness and position at the start of the first storm event of a wet season to collect a sample or samples of the storm water discharge during the first 3 hours of the discharge which will qualify as a valid "composite sample".

One way in which such valid grab and composite samples may be assured, of course, is to have persons standing by 24 hours a day during each and every day preceding the wet season in constant readiness to place storm water samplers in proper sampling positions immediately upon the start of each storm event to be monitored.

Obviously, this is an impractical solution to the storm water sampling problem. Moreover, there are numerous other solutions in which liquid sampling is desireable or essential and which involve essentially the same or other similar sampling problems and requirements as storm water sampling. Accordingly, there is a definite need for liquid sampling methods and devices for these and other sampling applications.

A variety of devices have been devised for sampling water and other liquids. Among the prior art disclosures of such sampling devices are the following:

U.S. Pat. No. 3,826,144, dated Jul. 30, 1974, to Wessels, describes a sampling device to be lowered into a liquid and having a valve which is opened manually to admit water to sample collection chambers in the device and float valves for sealing the chambers when full.

U.S. Pat. No. 3,929,003, dated Dec. 30, 1975, to LLewellyn describes apparatus for detecting materials in a liquid carrier, the apparatus utilizing a membrane for separating the material to be detected from the carrier liquid.

U.S. Pat. No. 4,271,704, dated Jun. 9, 1981, to Peters, describes a fluid sampling device to be lowered into fluid and having a valve which opens in response to external fluid pressure to admit fluid into the device.

U.S. Pat. No. 4,762,009, dated Aug. 9, 1988, to Scrudto, describes a device for measuring the suspended sediment in a flowing stream, the device having an upstream-facing funnel for directing water of the stream into a chamber in which the water is slowed sufficiently to effect settling of sediment in the water into a sample collection receptacle within the chamber.

U.S. Pat. No. 4,958,528, dated Sep. 25, 1990, to Garrison describes a runoff water sampling device having a valve which opens to admit runoff water to a sample collection chamber after a certain runoff water flow has occurred and a valve which closes to seal the chamber when full.

U.S. Pat. No. 5,069,878, dated Dec. 3, 1991, to Ehrenkranz describes a urine sampler having an upper bowl, a lower sample collection chamber, and an intervening specific-gravity-responsive valve.

U.S. Pat. No. 5,186,052, dated Feb. 16, 1993, to Gray, describes a storm water sampler including a basin with an elevated outlet to an underlying sewer.

U.S. Pat. No. 5,220,825, dated Jun. 22, 1993, to Peterson et al describes a particle sampler having a funnel for receiving settling particles in a body of water, and means for timed particle transfer from the funnel to a lower collection chamber.

U.S. Pat. No. 5,279,151, dated Jan. 18, 1994, to Coody et al describes sampling apparatus for a simulated rainfall test plot.

U.S. Pat. No. 5,347,877, dated Sep. 20, 1994, to Gadbois describes a storm water runoff sampler.

U.S. Pat. No. 5,408,892, dated Apr. 25, 1995, to Kawanami et al, describes a rainfall sampler.

Article entitled "Development of a Self-Sealing Rain Sampler for Arid Zones" by E. Adar et al, pages 592–596, vol 16, No. 3 , June 1980, of publication entitled "Water Resources Research" describes a rain sampler having an upper funnel, a lower collection chamber, and a float valve for sealing the chamber when filled.

SUMMARY OF THE INVENTION

This invention provides a novel liquid sampling apparatus which satisfies at least some requirements of the Industrial Storm Water Permitting Program and may be utilized to obtain storm water samples that comply with such requirements. Accordingly, the liquid sampling apparatus of the invention is ideally adapted for storm water sampling. In this regard, for example, the sampling apparatus may be placed in sampling position well before the onset of the wet season and remain there in total readiness, without human attention, to collect a storm water sample during the first storm event of the wet season.

While ideally suited for such storm water sampling, the liquid sampling apparatus of the invention is capable of other diverse liquid sampling applications, such as the leakage location application mentioned earlier and others. Accordingly, the sampling apparatus of the invention should not be regarded as limited to storm water sampling. The apparatus may be utilized to sample liquids flowing along virtually any type of liquid conductor including surfaces, open channels, or closed pipes or ducts and liquids which are either homogeneous liquids or mixtures of miscible or immiscible liquid components.

This invention provides liquid sampling apparatus including a number of basic components which may be assembled in several different combinations to provide a variety of different sampler configurations or liquid sampling devices. These basic components of the preferred liquid sampling apparatus of the invention include a cover having normally upper and lower sides and three receptacles of differing size referred to herein in places as small, intermediate, and large receptacles, respectively. The cover may be selectively mounted on the small and intermediate receptacles to form sample collection devices each having a liquid sample collection chamber. The intermediate and large receptacles are canisters which may be recessed into a floor, ground, or the like to form sumps for removably receiving a liquid sampling device of the invention.

The cover of the preferred sampling apparatus has an upwardly open basin at its upper side, a precise inlet passage opening through the floor of the basin into a sample collection chamber below the basin, and inlet valve means for controlling flow into the collection chamber through this inlet passage. In the described presently preferred inventive embodiment, this valve means is a ball float valve below the precise inlet passage which floats upwardly into contact with a valve seat about the lower end of the inlet passage to close the passage and seal the chamber as the water level in the chamber rises to fill the chamber. Sealing the chamber in this way prevents contamination and dilution of a collected sample in the chamber and escape of volatile components from the chamber. According to an important feature of this invention, the maximum spacing and hence maximum flow space between the valve ball and its valve seat is adjustable to vary the maximum flow rate into the collection chamber. The precise inlet passage is precisely sized to establish a water column of certain height and volume over the ball when the ball is nearly fully closed against its seat in order to assure proper flow past the ball into the chamber under this minimum flow condition.

The small receptacle of the liquid sampling apparatus is a sample collection container which can be releasably secured to the underside of the cover to form a first liquid sampling device according to the invention, referred to herein as a small liquid sampling device. This small sampling device can be placed in sampling position to collect a water sample within the container after which the container can be removed from the cover, capped, and transported to a laboratory for analysis without the necessity of transferring the sample to another container. The integrity of the collected sample is thereby preserved. The preferred sample collection container is a glass jar having an externally threaded neck at its upper end engagable in an internally threaded collar on the under side of the cover.

The intermediate receptacle of the present liquid sampling apparatus is a canister, referred to herein in places as a small canister, having a closed normally lower end and an open normally upper end circumferentially surrounded by a rim. This intermediate receptacle or canister is sized to receive the small sampling device of the invention with the cover of the small sampling device supported about its perimeter on a seat about the rim of the canister and with the sample container of the small sampling device suspended within the canister. The small sampling device and canister when thus assembled form a modified liquid sampling device according to the invention. The canister of this modified sampling device forms a holder or sump for the small sampling device.

The small receptacle or sample container of the modified liquid sampling device described above may be omitted to form a further modified liquid sampling device according to the invention referred to herein as a large liquid sampling device. In this large sampling device, the intermediate receptacle or canister of the liquid sampling apparatus is utilized as a sample container for containing the collected liquid sample. This modified liquid sampling device may be disposed in liquid sampling position in any convenient way that permits removal of the device including its sample container from the sampling site.

The large receptacle of the present liquid sampling apparatus is a canister having a closed normally lower end and an open normally upper end circumferentially surrounded by a rim and an upwardly facing seat about the rim. This large canister is sized to receive either of the modified sampling devices mentioned above and form a sump or holder for the sampling device.

DESCRIPTION OF THE PREFERRED EMBODIMENTS

Figure 1:
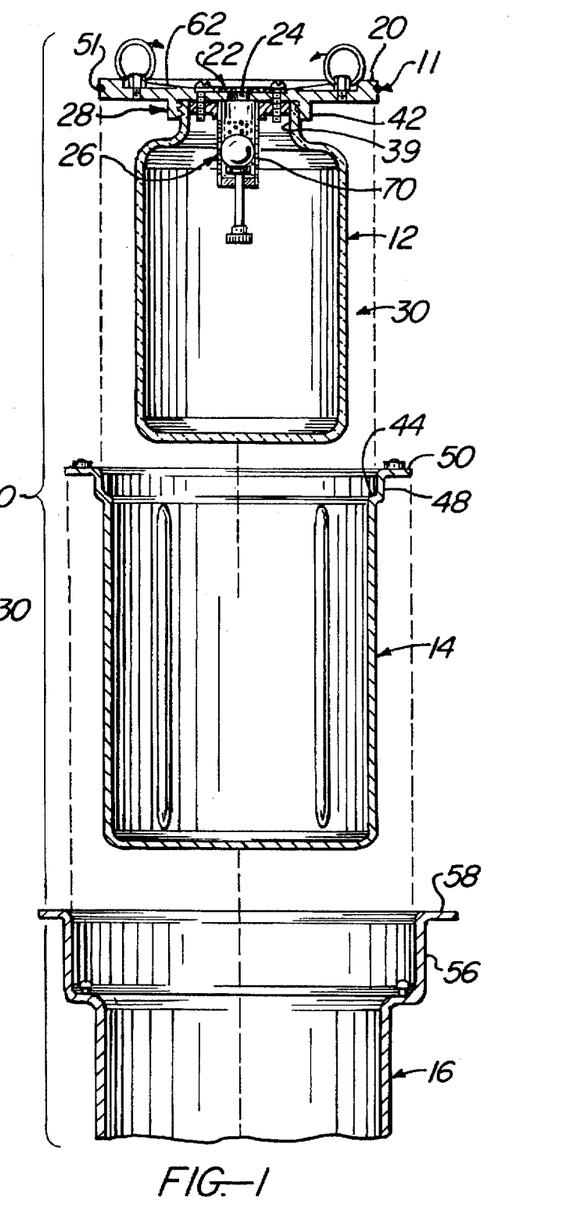
FIG. 1 is an exploded sectional view of an overall sampling apparatus according to the invention.
Figure 2:
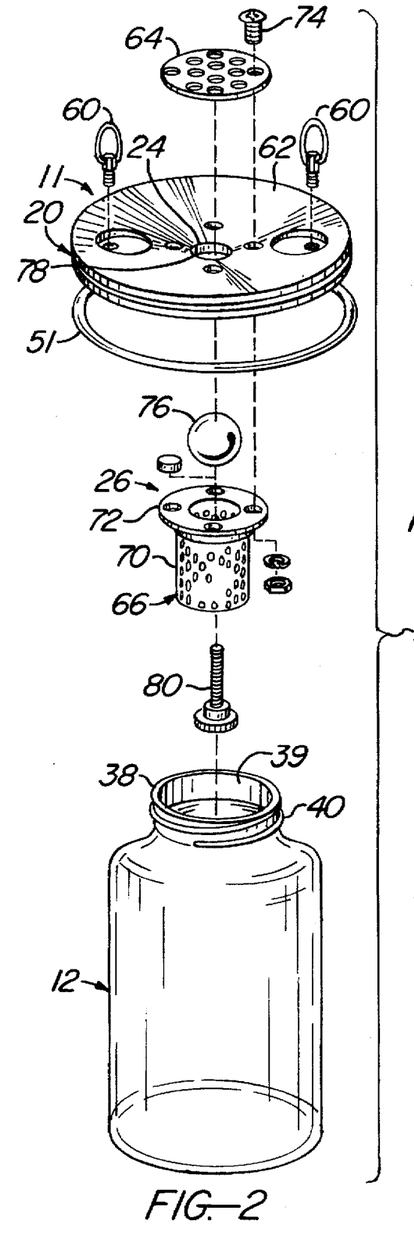
FIG. 2 is an exploded perspective view of a small sampling device according to the invention comprising certain components of the sampling apparatus in FIG. 1.

Turning now to these drawings and first to FIG. 1, there is illustrated a preferred liquid sampling apparatus 10 according to the invention. This liquid sampling apparatus comprises four basic components, namely a cover 11, a relatively small receptacle 12 which forms a sample collection container whose interior provides a sample collection chamber, an intermediate receptacle 14 in the form of a small canister, and a large receptacle 16 in the form of a large canister which forms a holder or sump for the sampler. The sample container 12, small canister 14, and sump 16 each have a normally upper open end and a normally lower closed end. As explained in more detail later, the sample container 12 is adapted to maintain the integrity of a collected sample by being capped after sample collection and used to transport a collected sample from the collection site to the laboratory for analysis without the necessity of transferring the sample to another container.

Cover 11 comprises a cover member 20 proper and inlet means 22 on the cover member. The inlet means 22 includes a precise inlet passage 24 extending through the center of the cover member, and valve means 26 for controlling flow through the passage in the manner explained later. Passage 24 has an upper end forming an inlet which opens to the upper side of the cover member and a lower end opening to the underside of the cover member.

Figures 3, 4, 5:
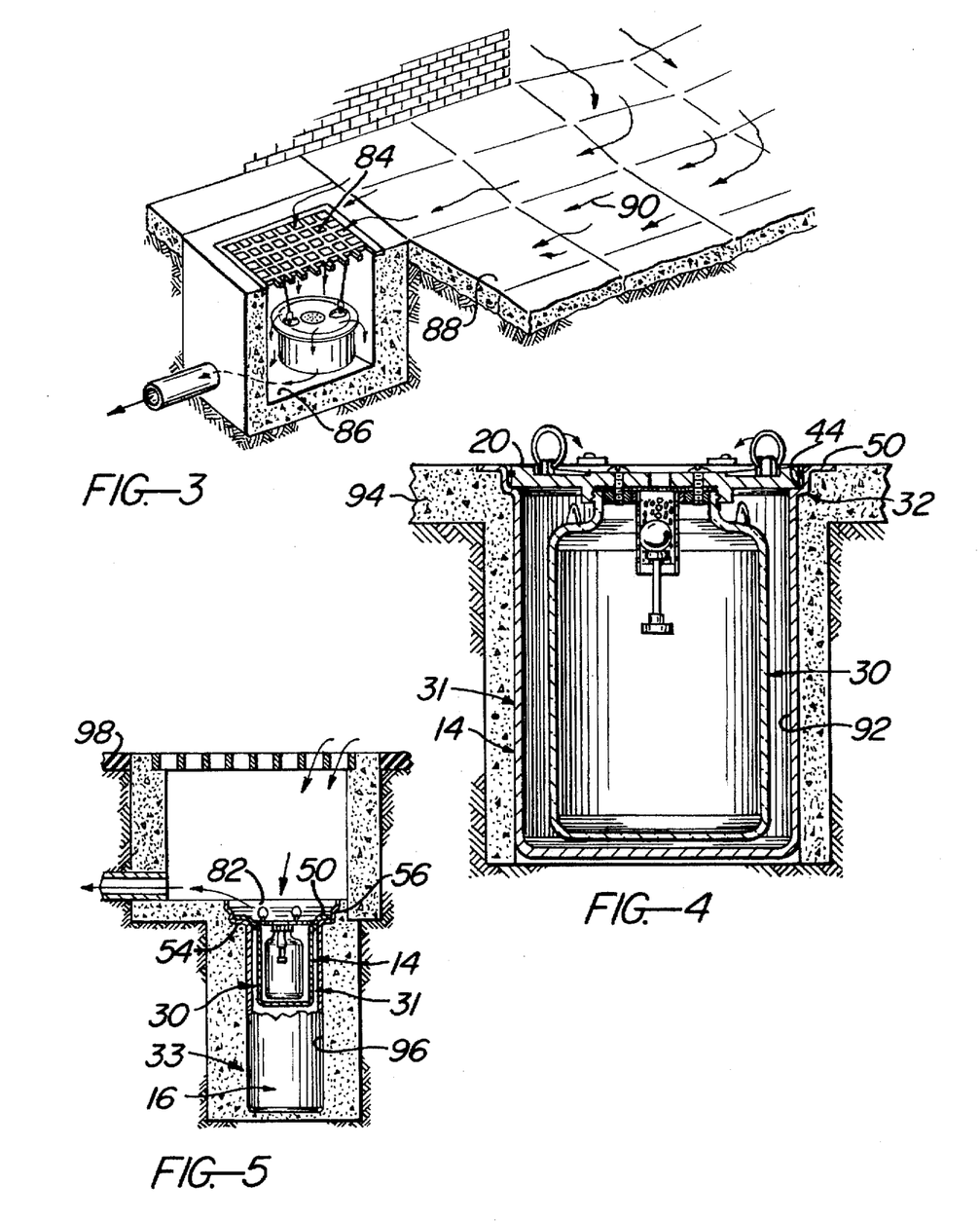
FIG. 3 illustrates the small sampling device of FIG. 2 in one possible liquid sampling position.
FIG. 4 is a vertical section through a modified sampling device according to the invention comprising certain components of the sampling apparatus in FIG. 1 and showing the device in one possible liquid sampling position.
FIG. 5 is a vertical section through the sampling apparatus in FIG. 1 showing the apparatus in one possible liquid sampling position.

The small receptacle or sample container 12 and the cover member 20 have releasably engagable means 28 for releasably coaxially securing the container to the normally underside of the cover member to form a first sampler configuration or sampling device 30 according to the invention hereafter referred to in places as a small liquid sampling device. When the cover and sample container are thus assembled, the cover member extends across and closes the top opening or mouth of the sample container. The precise cover passage 24 opens downwardly through this mouth to the interior collection chamber of the container. This small liquid sampling device 30 may be used by itself for sampling purposes, as illustrated in FIG. 3. Alternatively, the small liquid sampling device 30 may be assembled with the small canister 14 as shown in FIG. 4 to form a sampler configuration or sampling device 31 according to the invention in which the sampling device 30 is removably supported within the small canister. The small canister 14 then forms a holder or sump for the sampling device 30 which may be embedded in a floor or the ground, as shown in FIG. 4. The cover member 20 extends across and closes the open top of the small canister. The small canister or sump 14 and the cover member 20 have engagable means 32 which releasably retain these parts in their assembled relation. The sampling device 31 and the large canister 16 may be assembled in the manner shown in FIG. 5 to form a sampler configuration or sampling device 33 according to the invention. The sampling device 31 is removably supported within the large canister 16 by engagable means 34 on the canisters 14, 16. The large canister may be embedded in a floor or the ground, as shown, to form a holder or sump for the sampling device 31.

Figure 6:
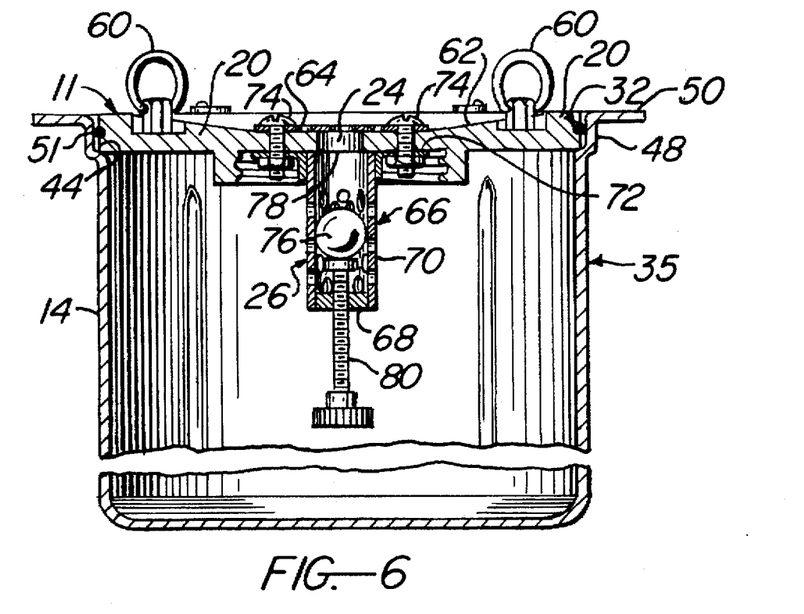
FIG. 6 is a longitudinal section through a further modified sampling device according to the invention comprising certain components of the sampling apparatus in FIG. 1.
Figure 7:
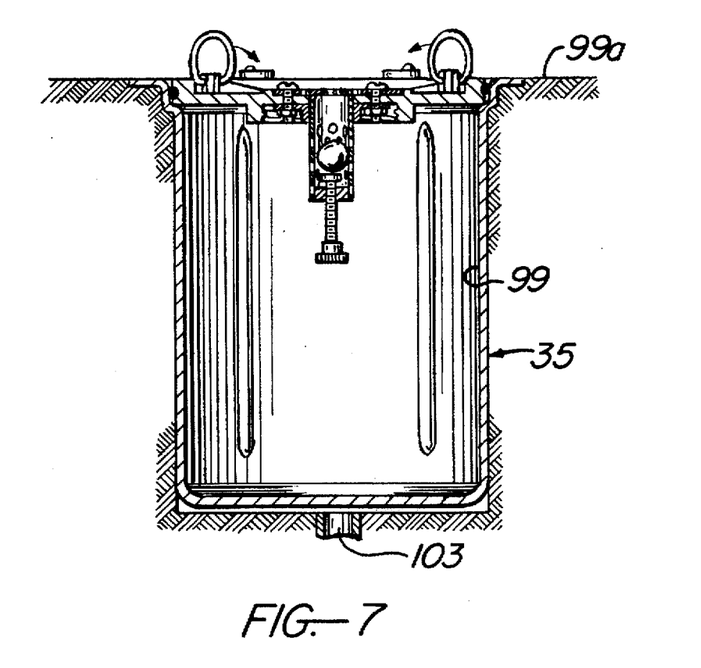
FIG. 7 illustrates the sampling device of FIG. 6 in one possible liquid sampling position.
Figure 8:
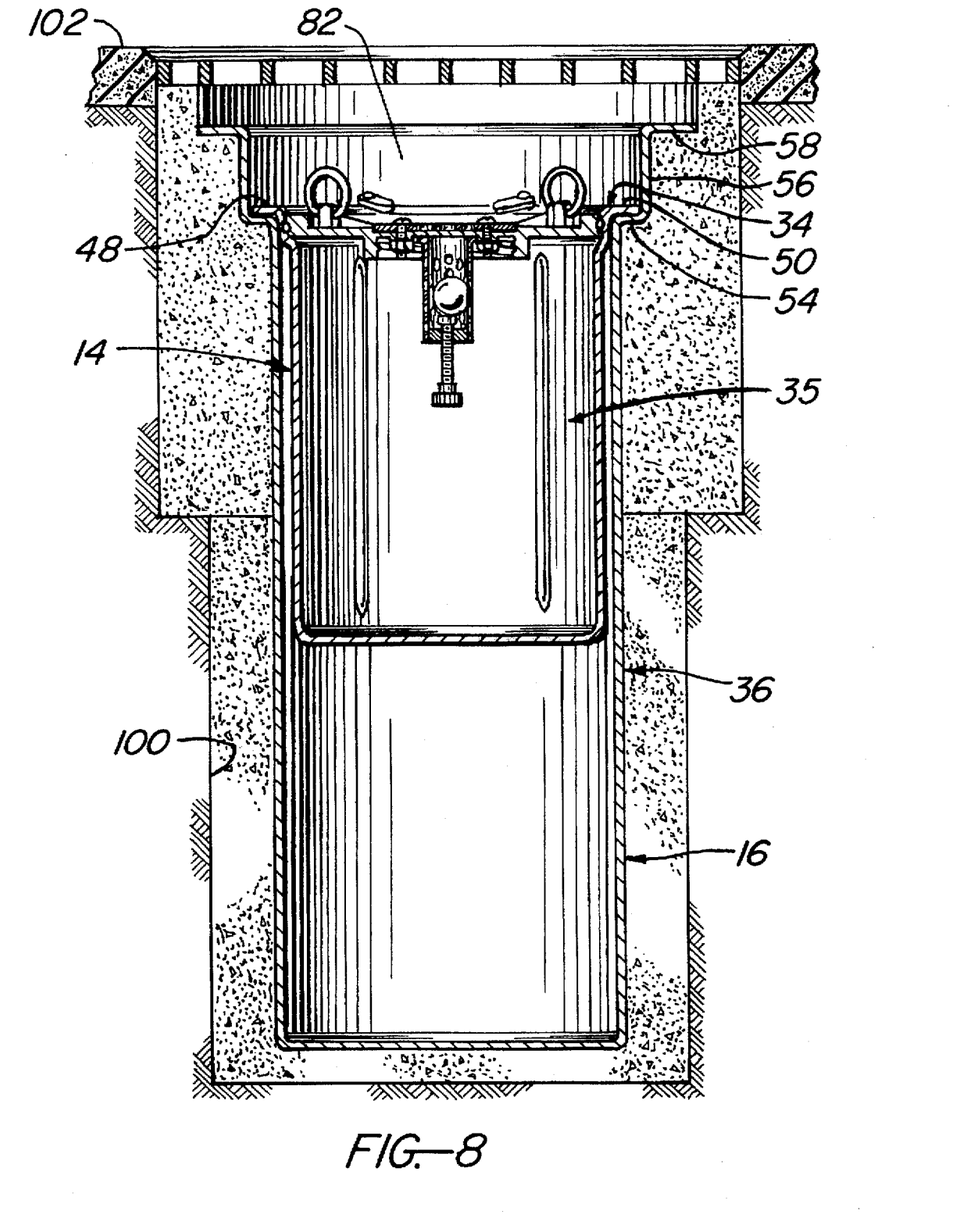
FIG. 8 is a longitudinal section through a further modified sampling device according to the invention comprising certain components of the sampling apparatus in FIG. 1 and showing the apparatus in one possible sampling position.

The cover 11 and small canister 14 may be assembled in the manner illustrated in FIGS. 6 and 7 to form a sampler configuration or sampling device 35 according to the invention referred to herein as a large sampling device. This large sampling device omits the sample container 12 and utilizes the canister 14 as a sample container. The cover member 20 is removably supported on the canister 14 by the engagable means 32 on the cover member and canister and extends across and closes the top opening of this canister. As explained later, the canister 14 may have locking means for releasably locking the cover member 20 to the canister. The cover passage 24 opens downwardly into the interior of the canister 14. The large liquid sampling device 35 may be used for sampling purposes by itself, as by removably positioning the device within a cavity in the ground or floor having a bottom drain hole, as shown in FIG. 7. Alternatively, the large sampling device 35 may be placed within the large canister 16, as shown in FIG. 8, to form a sampler configuration or sampling device 36 according to the invention in which the large canister forms a holder or sump for the sampling device 35 which may be embedded in a floor or the ground. In this embodiment, the canister 14 of the large sampling device 35 is removably supported within the large canister 16 by the engagable means 34 on these canisters.

Referring now in more detail to the drawings, the preferred sample container 12 is a glass jar having an upper reduced neck 38 surrounding the open mouth 39 of the jar. The engagable means 28 releasably securing this sample container or jar to the cover member 20 comprises external threads 40 about the jar neck 38 and a coaxial internally threaded collar 42 on the under side of the cover member for threadedly receiving the threaded jar neck. The cover passage 24 extends through the cover member 20 on the axis of the collar 42.

Small canister 14 is a relatively thin-walled, cylindrical cup-shaped part preferably fabricated from stainless steel. The upper open end of this canister is internally diametrically sized to receive the cover member 20. Engagable means 32 which retain the cover member 20 and the small canister 14 in their assembled relation in the several sampler configurations or sampling devices 31, 33, 35, 36 of FIGS. 4–8 comprise a radially narrow outwardly directed annular flange 44 about the upper open end of the small canister 14 forming an upwardly facing annular seat engagable by a circumferential portion of the cover member to vertically support the cover member in the small canister. About the perimeter of the flange 44 is an upstanding annular wall 48. At the upper end of the wall 48 is an outwardly directed annular flange 50. The cover member 20 is sized in diameter to fit snugly but removably within the upper wall portion 48 of the canister 14 with the perimeter of the cover member resting on the seat 44. Contained within a groove in the circumferential edge of the cover member 20 is a seal ring 51 which engages the wall 48 to seal the cover member to the canister 14. As discussed later, it may be desirable or essential in some cases to secure the cover member 20 to the canister 14 by positive acting releasable connecting means.

Large canister 16 is a relatively thin-walled, cylindrical cup-shaped part, preferably fabricated from stainless steel, which receives the small canister 14 in the sampler configurations or sampling devices 33 and 36 of FIGS. 5 and 8. As shown best in FIG. 8, the large canister 16 is internally diametrically sized to slidably receive the upper wall portion 48 of the small canister 14. Engagable means 34 which retain the two canisters in their assembled relation of FIGS. 5 and 8 comprises the upper outwardly directed flange 50 on the small canister and an outwardly directed annular flange 54 about the open upper end of the large canister 16 forming an upwardly facing annular seat engagable by the small canister flange 50 to support the small canister vertically in the large canister. About the outer perimeter of the large canister flange 54 is an upstanding annular wall 56 terminating at its upper end in an outwardly directed flange 58.

The cover member 20 is a rigid disc preferably fabricated from poly vinyl chloride (PVC). Attached to the upper side of the cover member are a pair of rings 60 by which the member may be held. The upper side of the cover member is arcuately recessed to form a shallow basin 62 having its lowest point at the center of the cover member. The upper, radially outer circumferential edge of the cover member forms a rim about and above the low central point of the basin. The upper end of the cover passage 24 forms a passage inlet which opens to the basin 62 at this central low point. A perforated grate 64 overlies this passage inlet to block entrance of debris into the passage.

The valve means 26 for controlling liquid flow through the cover passage 24 comprises a perforated cylindrical cage 66 coaxially positioned at the underside of the cover member 20. This cage has a bottom end wall 68, a perforated cylindrical sidewall 70, and an open top end circumferentially surrounded by an outwardly directed flange 72. Flange 72 seats against the under side of the cover member 20 about the lower end of the cover passage 24 so that the passage opens to the interior of the cage. The grate 64 and cage 66 are secured to the cover member by fasteners 74 which extend through the grate, cover member, and the cage flange 72. Freely movable within the cage 66 is a float valve member 76 in the form of a buoyant ball. This valve ball is movable upwardly in the cage 66 to a closed position in which it engages a valve seat 78 about the lower end of the cover passage 24 to close the passage. Gravity urges the ball downwardly in the cage away from its seat 78 to open the passage. An adjustable stop screw 80 is axially threaded in the lower cage end wall 68 to limit opening movement of the valve ball. This stop screw serves as an open stop for the valve ball and is adjustable to adjust the maximum effective flow space between the valve ball 76 and its seat 78.

It is now evident that the four components of the present liquid sampling apparatus 10, that is the cover 11, the sample container or jar 12, the small canister 14, and the large canister 16 may be assembled in various combinations to provide the variety of liquid sampler configurations or sampling devices 30, 31, 33, 35, 36 illustrated in FIGS. 1, 4, 5, 6–7, and 8. As discussed later, each sampling device is adapted to be placed in a sampling position such that the sampling device is disposed to receive the liquid to be sampled.

In FIG. 1, the cover 11 is threadedly secured to the top of the glass sample container 12 with the valve cage 70 extending downwardly though the open mouth 39 of the container into its interior sample collection chamber to form the small liquid sampling device 30. In FIG. 4, the small sampling device 30 is removably supported within the small canister 14 with the cover member 20 of the small sampling device resting on the internal shoulder 44 of the small canister to form the liquid sampling device 31. The small canister 14 supports, encloses and provides a protective housing or sump for the small sampling device 30. In FIG. 5, the sampling device 31 of FIG. 4 is removably supported within the large canister 16 with the upper flange 50 of the small canister 14 resting on the upper shoulder 54 of the large canister 16 to form the sampling device 33. The large canister 16 supports, encloses and provides a protective housing or sump for the sampling device 31. In FIGS. 6 and 7, the cover 11 by itself, that is without the glass sample container or jar 12, is removably supported in the small canister 14 in the same manner as in the sampling devices 31 and 33 to form the large liquid sampling device 35. This large liquid sampling device is identical to the sampling device 31 except for the omission of the glass sample container 12 and the fact that the interior of the small canister 14 forms a liquid collection chamber. In FIG. 8, the large sampling device 35 is removably supported in the large canister 16 with the flange 50 of the small canister 14 resting on the internal shoulder 54 of the large canister to form the sampling device 36. In both the sampling device 33 of FIG. 5 and the sampling device 36 of FIG. 8, the upper wall portion 56 of the large canister 16 projects above the cover member 11 to form an upstanding rim about the cover member and thereby form a relatively deep basin 82 at the upper end of the sampler having a floor formed by the cover member 20 and an upstanding rim formed by the upper edge of wall portion 56.

It is evident at this point that the canister 16 is intended to be used only in combination with the intermediate container 14. In this regard, it will be seen in FIGS. 4, 5 and 8 that the cover 11 is sized to fit within the upper end of the intermediate container 14 above the internal shoulder 44 of this container with the periphery of the cover sealed to the inner surface of the upper annular wall or rim 48 of the container 14. The container 14, in turn, is sized to fit within the open upper end of the canister 16 with the upper flange 50 of the container 14 seating on the upper interior canister shoulder 54 to vertically support the container 14 in the canister and with the upper rim 48 of the container 14 fitting within the upper end of the canister 16 just below the canister shoulder 54, as clearly shown in the drawings. Since the cover 11 fits within and is circumferentially surrounded by the container rim 48 and this rim, in turn, fits within and is circumferentially surrounded by the cylindrical wall of the canister 16 below the canister shoulder 54, the cover 11 is too small in diameter to be directly supported on this canister shoulder. Accordingly, it is impossible to support the cover 11 directly in the upper end of the canister 16 with the cover resting on the canister shoulder 54. The purpose of the intermediate container 14 in the sampler combinations of FIGS. 1 and 5 and also FIG. 8 is to support the cover 11 in the open upper end of the canister 16 with the cover located at the lower end of the upper canister rim 56 so as to form with this rim the deep sampler basin 82.

In use, the sampling devices 30, 31, 33, 35, and 36 are placed in appropriate sampling positions to receive the water or other liquid to be sampled in such a way that the liquid enters their upper basin 62, 82, as the case may be, and then drains from the basin through the cover inlet passage 24 into the underlying sample collection receptacle, i.e. the glass sample collection jar 12 or the small canister 14, as the case may be. FIG. 3, for example, illustrates the small sampling device 30 disposed in one possible sampling position in which the device is suspended by its cover rings 60 from the underside of a grating 84 overlying a sump 86 entering a liquid drainage surface 88, such as a floor, driveway, the ground, or any other surface along which flows or drains the water or other liquid 90 to be sampled. In FIG. 4, the canister or sump 14 of the sampling device 31 is positioned, either removably or permanently, within a concrete lined sump 92 in a liquid drainage surface 94. In FIG. 5, the canister or sump 16 of the sampling device 33 is positioned, either removably or permanently, within a concrete lined sump 96 in a liquid drainage surface 98. In FIG. 7, the large liquid sampling device 35 is removably positioned within a concrete lined sump 99 in a liquid drainage surface 99a. In FIG. 8, the canister or sump 16 of the sampling device 36 is positioned within a concrete lined sump 100 in a liquid drainage surface 102. In each case where the sampling device is removably positioned within a concrete sump or the like, the sump may have a bottom drain hole, such as drain hole 103 in FIG. 7.

The float valve ball 76 of each liquid sampling device 30, 31, 33, 35, and 36 is initially in its illustrated lower open position against the stop screw 80 to permit liquid inflow through the cover passage 24 into the sample collection chamber in the respective sample collection receptacle 12 or 14. Assuming that sufficient liquid enters the collection chamber to fill the latter, the rising liquid level in the chamber will eventually raise the valve ball 76 into contact with its valve seat 78 to close the passage 24 and thereby seal the collection chamber against both dilution of the collected liquid sample and escape from the chamber of volatile elements present in the collected sample.

The valve stop screw 80 is adjustable to adjust the maximum opening movement of the valve ball 76 and thereby the maximum flow space between the ball and its valve seat 78. This adjustment is effective to adjust the maximum flow rate at which liquid may enter the collection chamber and hence the overall time duration of the sampling operation. When the stop screw 80 is set to hold the valve ball 76 in an upper nearly closed position, wherein a very small clearance exists between the valve ball and its valve seat 78 to provide a very low maximum liquid inflow rate into the collection chamber, it is necessary to maintain a sufficient liquid head at a precise volume above the ball to assure continued liquid inflow into the collection chamber at an accurately controlled flow rate. In the illustrated preferred sampling apparatus of the invention, the required liquid head and precise liquid volume above the valve ball 76 is assured by providing the cover passage with a diameter of 1.00 inches and providing the cover member with sufficient thickness at the wall of the cover passage 24 to provide the passage with an axial length of at least one inch.

After a sample has been collected in the sample collection receptacle, the collection receptacle is transported from the collection site to a laboratory where the sample is analyzed. In the case of the sampling device 30 of FIG. 3, this is preferably accomplished by removing the cover 11 from the sample jar 12, capping the jar, i.e. sealing the jar with a separate sealing cap (not shown), and transporting the capped jar to the laboratory. Alternatively, the entire sampler 30 can be transported from the sampling site to the laboratory with the ball valve 76 held closed either by adjustment of the valve stop screw 80 or by the collected sample filling the sample jar. In the case of the sampling devices 31 of FIG. 4, the small sampler 30 is removed from its surrounding canister or sump 14 after which the collected sample is carried to the laboratory in the sample jar in either of the ways described above in connection with FIG. 3. In the case of the sampling device 33 of FIG. 5, the entire liquid sampler 31 including its sample jar 12 containing the collected sample can be removed from the large canister or sump 16 and transported to the laboratory with the collected sample sealed within the sample jar by the valve ball 76 as described above in connection with FIG. 3. Alternatively, the sampler 30 may be removed from the inner canister or sump 14 and the sample transported to the laboratory in either of the two ways mentioned above in connection with FIG. 3. In the case of the sampling device 35 of FIGS. 6 and 7, the entire large sampler is removed from the sampling site and carried to the laboratory. Finally, in the case of the sampling device 36 of FIG. 8, the sampler 35 is removed from the surrounding large canister or sump 16 and transported to the laboratory.

Figure 9:
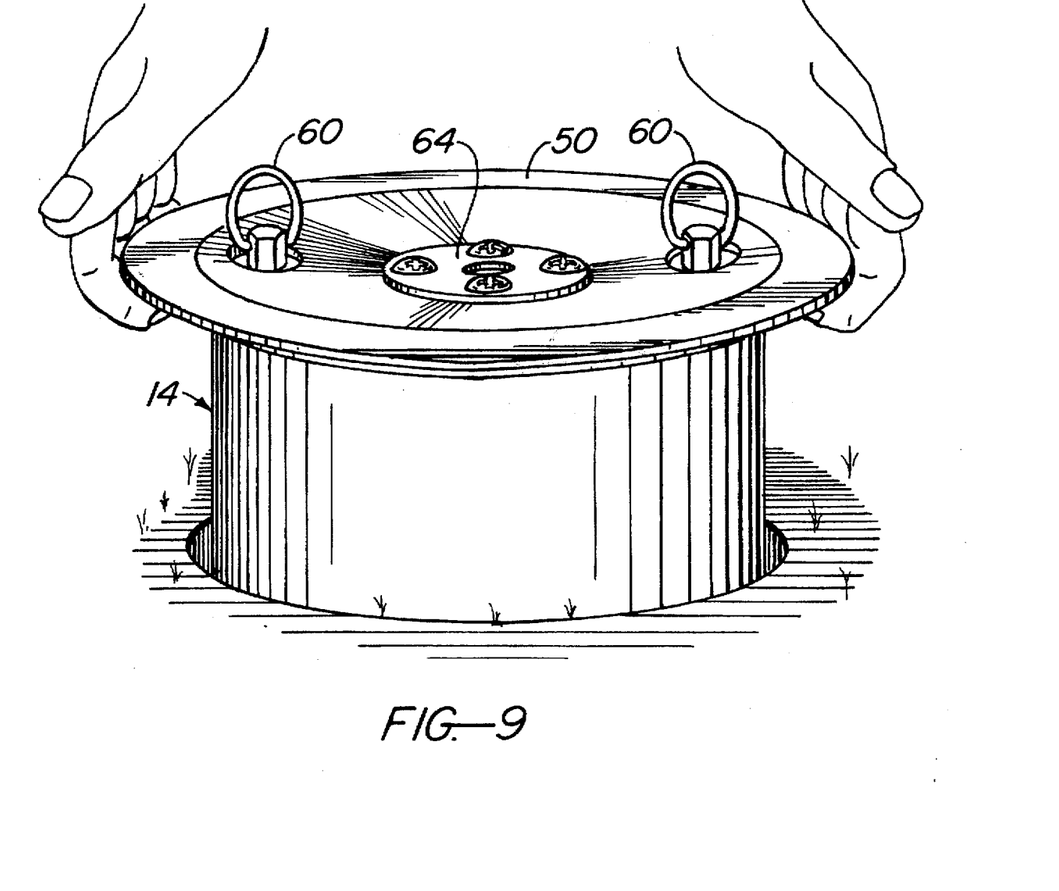
FIG. 9 illustrates the manner in which the liquid sampling device of FIG. 7 is lowered into and raised from its sump.

It is evident from the foregoing description that this invention contemplates the possibility of always using the liquid sampling device 30 for liquid sample collection, i.e. always collecting liquid samples within the glass jar 12 of the sampling device 30, and using the small canister 14 only as a holder or sump for the liquid sampling device 30, as shown in FIGS. 4 and 5, and never as a liquid sample container. In this case, since the glass jar 12 is firmly secured by the coupling means 28 to the cover 11 of the sampling device 30, this sampling device may be safely held, handled, and lowered into and raised from the sump 14 in FIG. 4 and from both sumps 14, 16 in FIG. 5 without any risk of loss of integrity of the collected sample by grasping the cover rings 60 (in the manner illustrated in FIG. 9). The cover member 20 may have a sufficiently snug fit in the upper end of the canister or sump 14 to prevent the latter from separating from the cover member when the sampling device 31 is held by its cover rings 60 and thereby permit the sampling device 31 to be lowered into and raised from the large canister or sump 16 in FIG. 5 as a single unit by holding the sampler cover rings 60. Preferably, however, the cover member 20 is positively but releasably locked to the canister 14 to positively secure against separation the cover member and canister not only of the sampling device 30 but more importantly of the sampling device 35 in FIGS. 6–8 in which the canister 14 is utilized as the sample collection receptacle. To this end, the upper flange 50 of canister 14 mounts pivoted clamps 104 (FIG. 9) which are rotatable between their solid line retracted positions in which the clamps permit removal of the cover 11 from the canister 14 and their broken line locking positions in which the clamps positively lock the cover to the canister 14. When the cover 11 is thus positively locked to the canister 14, the sample collection device 31 may be safely and conveniently held and handled by its cover rings 60 and lowered into and raised from its sump 16 in FIG. 5. Likewise, the sample collection device 35 may be safely and conveniently held and handled and lowered into and raised from its sump 99 in FIGS. 7 and 9 by grasping its cover rings 60, as shown in FIG. 9.

The inventor claims:

1. Liquid sampling apparatus comprising:
   a first receptacle having an open upper end and a lower end,
   a second receptacle having an open upper end and a lower end,
   a cover including a cover member having upper and lower sides and forming an upwardly opening basin for receiving a liquid to be sampled, and a passage extending through said cover member and opening to said basin and through the lower side of the cover member,
   first releasably engaging means on said cover member and said first receptacle releasably joining said cover and said first receptacle in assembled relation wherein (a) the upper end of said first receptacle is releasably secured to the lower side of said cover member, (b) said cover member extends laterally beyond the upper end of said first receptacle, whereby the cover member has a circumferential portion about and laterally beyond the upper end of the first receptacle, and (c) said passage opens to the interior of said first receptacle through the upper end of said first receptacle,
   second releasably engaging means on said cover member and said second receptacle releasably retaining said cover and said second receptacle in assembled relation wherein (a) said cover member extends across and closes the open upper end of the second receptacle, (b) said circumferential portion of said cover member engages said second receptacle about the upper end of said second receptacle, (c) said first receptacle depends from the lower side of said cover member into the interior of said second receptacle through the open upper end of said second receptacle, and (d) said first and second receptacles and said cover form a first liquid sampling device adapted to be placed in a sampling position wherein said basin is disposed to receive a liquid to be sampled and said second receptacle forms a sump removably receiving the assembled cover and first receptacle, and wherein
   said cover and said first receptacle may be assembled in said assembled relation of said cover and first receptacle without said second receptacle to form a second liquid sampling device comprising only said cover and said first receptacle and adapted to be placed in a sampling position wherein said basin is disposed to receive a liquid to be sampled, and
   said cover and said second receptacle may be assembled in said assembled relation of said cover and said second receptacle without said first receptacle to form a third liquid sampling device comprising only said cover and said second receptacle and adapted to be placed in a sampling position wherein said basin is disposed to receive a liquid to be sampled.

2. Liquid sampling apparatus according to claim 1 wherein:
   the upper side of said cover member is substantially flush with the upper end of said second receptacle in said assembled relation of said cover and second receptacle,
   said upper side of said cover member is recessed to form said basin, and
   said liquid sampling apparatus further comprises a third receptacle having an open upper end and a lower end, and releasably engaging means on said second and third receptacles releasably supporting said first sampling device in assembled relation with said third receptacle wherein (a) said first sampling device is removably positioned within and closes the upper end of said third receptacle, (b) the upper end of said third receptacle extends about and above the upper side of said cover member, and (c) the assembled first sampling device and third receptacle form a fourth sampling device adapted to be placed in a sampling position wherein said basin is disposed to receive a liquid to be sampled.

3. Sampling apparatus according to claim 1 wherein:
   said first receptacle comprises a glass jar having a neck at said upper end of said first receptacle, and
   said first releasably engaging means comprise external threads about said neck of said glass jar, and an internally threaded portion on the lower side of said cover member threadably receiving said jar neck.

4. Sampling apparatus according to claim 1 wherein:
   said second receptacle comprises a canister having an upper end opening, and
   said second releasably engaging means comprises said circumferential portion of said cover member and an upwardly facing shoulder about said upper end opening for seating said circumferential portion of said cover member.

5. Sampling apparatus according to claim 1 wherein:
   said first receptacle comprises a glass jar having a neck at said upper end of said first receptacle,
   said first releasably engaging means comprise external threads about said neck of said glass jar, and an internally threaded portion on the lower side of said cover member threadably receiving said jar neck,
   said second receptacle comprises a canister having an upper end opening, and
   said second releasably engaging means comprises said circumferential portion of said cover member and an upwardly facing shoulder about said upper end opening for seating said circumferential portion of said cover member.

6. Sampling apparatus according to claim 5 wherein:
   the upper side of said cover member is substantially flush with the upper end of said second receptacle in said assembled relation of said cover and second receptacle, said upper side of said cover member is recessed to form said basin, and said liquid sampling apparatus further comprises a third receptacle having an open upper end and a lower end, and releasably engaging means on said second and third receptacles releasably supporting said first sampling device in assembled relation with said third receptacle wherein (a) said first sampling device is removably positioned within and closes the upper end of said third receptacle, (b) the upper end of said third receptacle extends about and above the upper side of said cover member, and (c) the assembled first sampling device and third receptacle form a fourth sampling device adapted to be placed in a sampling position wherein said basin is disposed to receive a liquid to be sampled.

7. Sampling apparatus according to claim 6 wherein:

said third receptacle comprises a canister having an upper end opening, and said third releasably engaging means comprises an outwardly directed flange about said upper end opening of said second receptacle canister, and an internal upwardly facing shoulder about said upper end opening of said third receptacle canister for seating on said flange.

8. Sampling apparatus according to claim 1 wherein:

said cover includes adjustable valve means for controlling liquid flow through said cover passage.

9. Liquid sampling apparatus comprising:

a first receptacle having an open upper end and a lower end, a second receptacle having an open upper end and a lower end, a cover including a cover member having upper and lower sides and forming an upwardly opening basin for receiving a liquid to be sampled, and a passage extending through said cover member and opening in said basin and through the lower side of the cover member, first releasably engaging means on said cover member and said first receptacle releasably joining said cover and said first receptacle in assembled relation wherein (a) the upper end of said first receptacle is releasably secured to the lower side of said cover member, (b) said cover member extends laterally beyond the upper end of said first receptacle, whereby the cover member has a circumferential portion about and laterally beyond the upper end of the first receptacle, and (c) said passage opens to the interior of said first receptacle through the upper end of said first receptacle, second releasably engaging means on said cover member and said second receptacle releasably retaining said cover and said second receptacle in assembled relation wherein (a) said cover member extends across and closes the open upper end of the second receptacle, (b) said circumferential portion of said cover member engages said second receptacle about the upper end of said second receptacle, (c) said first receptacle depends from the lower side of said cover member into the interior of said second receptacle through the open upper end of said second receptacle, and (d) said first and second receptacles and said cover form a first liquid sampling device adapted to be placed in a sampling position wherein said basin is disposed to receive a liquid to be sampled and said second receptacle forms a sump removably receiving the assembled cover and first receptacle, and wherein said cover and said first receptacle may be assembled in said assembled relation of said cover and first receptacle without said second receptacle to form a second liquid sampling device comprising only said cover and said first receptacle and adapted to be placed in a sampling position wherein said basin is disposed to receive a liquid to be sampled, said cover and said second receptacle may be assembled in said assembled relation of said cover and said second receptacle without said first receptacle to form a third liquid sampling device comprising only said cover and said second receptacle and adapted to be placed in a sampling position wherein said basin is disposed to receive a liquid to be sampled, said cover member has a recess in the upper side of said cover member forming said basin, and said cover includes valve means for controlling flow through said cover passage comprising a perforate valve cage extending below said cover member and having an upper end secured to said cover member about said cover passage with the interior of the cage opening to said cover passage, a valve seat about said passage, a float valve in said cage movable upwardly into contact with said valve seat to close said passage and downwardly away from said valve seat to open said passage, and adjustable stop means on said cage for adjustably limiting downward opening movement of said float valve away from said valve seat to adjust the maximum flow space between said valve seat and said float valve.

10. Liquid sampling apparatus comprising:

a first receptacle having an open upper end and a lower end, a second receptacle having an open upper end and a lower end, a cover including a cover member having upper and lower sides and forming an upwardly opening basin for receiving a liquid to be sampled, and a passage extending through said cover member and opening in said basin and through the lower side of the cover member, first releasably engaging means on said cover member and said first receptacle releasably joining said cover and said first receptacle in assembled relation wherein (a) the upper end of said first receptacle is releasably secured to the lower side of said cover member, (b) said cover member extends laterally beyond the upper end of said first receptacle, whereby the cover member has a circumferential portion about and laterally beyond the upper end of the first receptacle, and (c) said passage opens to the interior of said first receptacle through the upper end of said first receptacle, second releasably engaging means on said cover member and said second receptacle releasably retaining said cover and said second receptacle in assembled relation wherein (a) said cover member extends across and closes the open upper end of the second receptacle, (b) said circumferential portion of said cover member engages said second receptacle about the upper end of said second receptacle, (c) said first receptacle depends from the lower side of said cover member into the interior of said second receptacle through the open upper end of said second receptacle, and (d) said first and second receptacles and said cover form a first liquid sampling device adapted to be placed in a sampling position wherein said basin is disposed to receive a liquid to be sampled and said second receptacle forms a sump removably receiving the assembled cover and first receptacle, and wherein said cover and said first receptacle may be assembled in said assembled relation of said cover and first receptacle without said second receptacle to form a second liquid sampling device comprising only said cover and said first receptacle and adapted to be placed in a sampling position wherein said basin is disposed to receive a liquid to be sampled, said cover and said second receptacle may be assembled in said assembled relation of said cover and said second receptacle without said first receptacle to form a third liquid sampling device comprising only said cover and said second receptacle and adapted to be placed in a sampling position wherein said basin is disposed to receive a liquid to be sampled, said first receptacle comprises a glass jar having a neck at said upper end of said first receptacle, said first releasably engaging means comprise external threads about said neck of said glass jar, and an internally threaded portion on the lower side of said cover member threadably receiving said jar neck, said second receptacle comprises a canister having an upper end opening, said second releasably engaging means comprises said circumferential portion of said cover member and an upwardly facing shoulder about said upper end opening for seating said circumferential portion of said cover member, and said cover includes at least one of the following: (a) a recess in the upper side of said cover member forming said basin, (b) adjustable valve means for controlling liquid flow rate through said cover passage and closing said passage in response to filling of the respective sampling device which includes the cover with a certain volume of the liquid being sampled.

11. Liquid sampling apparatus comprising:

a first receptacle having an open upper end and a lower end, a second receptacle having an open upper end and a lower end, a cover including a cover member having upper and lower sides and forming an upwardly opening basin for receiving a liquid to be sampled, and a passage extending through said cover member and opening in said basin and through the lower side of the cover member, first releasably engaging means on said cover member and said first receptacle releasably joining said cover and said first receptacle in assembled relation wherein (a) the upper end of said first receptacle is releasably secured to the lower side of said cover member, (b) said cover member extends laterally beyond the upper end of said first receptacle, whereby the cover member has a circumferential portion about and laterally beyond the upper end of the first receptacle, and (c) said passage opens to the interior of said first receptacle through the upper end of said first receptacle, second releasably engaging means on said cover member and said second receptacle releasably retaining said cover and said second receptacle in assembled relation wherein (a) said cover member extends across and closes the open upper end of the second receptacle, (b) said circumferential portion of said cover member engages said second receptacle about the upper end of said second receptacle, (c) said first receptacle depends from the lower side of said cover member into the interior of said second receptacle through the open upper end of said second receptacle, and (d) said first and second receptacles and said cover form a first liquid sampling device adapted to be placed in a sampling position wherein said basin is disposed to receive a liquid to be sampled and said second receptacle forms a sump removably receiving the assembled cover and first receptacle, and wherein said cover and said first receptacle may be assembled in said assembled relation of said cover and first receptacle without said second receptacle to form a second liquid sampling device comprising only said cover and said first receptacle and adapted to be placed in a sampling position wherein said basin is disposed to receive a liquid to be sampled, said cover and said second receptacle may be assembled in said assembled relation of said cover and said second receptacle without said first receptacle to form a third liquid sampling device comprising only said cover and said second receptacle and adapted to be placed in a sampling position wherein said basin is disposed to receive a liquid to be sampled, said first receptacle comprises a glass jar having a neck at said upper end of said first receptacle, said first releasably engaging means comprise external threads about said neck of said glass jar, and an internally threaded portion on the lower side of said cover member threadably receiving said jar neck, said second receptacle comprises a canister having an upper end opening, said second releasably engaging means comprises said circumferential portion of said cover member and an upwardly facing shoulder about said upper end opening for seating said circumferential portion of said cover member, said cover member has a recess in the upper side of said cover member forming said basin, and said cover includes valve means for controlling flow through said cover passage comprising a perforate valve cage extending below said cover member and having an upper end secured to said cover member about said cover passage with the interior of the cage opening to said cover passage, a valve seat about said passage, a float valve in said cage movable upwardly into contact with said valve seat to close said passage and downwardly away from said valve seat to open said passage, and adjustable stop means on said cage for adjustably limiting downward opening movement of said float valve away to adjust the maximum flow space between said valve seat and said float valve.

12. Liquid sampling apparatus comprising:

a first receptacle having an open upper end and a lower end, a second receptacle having an open upper end and a lower end, a cover including a cover member having upper and lower sides and forming an upwardly opening basin for receiving a liquid to be sampled, and a passage extending through said cover member and opening in said basin and through the lower side of the cover member, first releasably engaging means on said cover member and said first receptacle releasably joining said cover and said first receptacle in assembled relation wherein (a) the upper end of said first receptacle is releasably secured to the lower side of said cover member, (b) said cover member extends laterally beyond the upper end of said first receptacle, whereby the cover member has a circumferential portion about and laterally beyond the upper end of the first receptacle, and (c) said passage opens to the interior of said first receptacle through the upper end of said first receptacle, second releasably engaging means on said cover member and said second receptacle releasably retaining said cover and said second receptacle in assembled relation wherein (a) said cover member extends across and closes the open upper end of the second receptacle, (b) said circumferential portion of said cover member engages said second receptacle about the upper end of said second receptacle, (c) said first receptacle depends from the lower side of said cover member into the interior of said second receptacle through the open upper end of said second receptacle, and (d) said first and second receptacles and said cover form a first liquid sampling device adapted to be placed in a sampling position wherein said basin is disposed to receive a liquid to be sampled and said second receptacle forms a sump removably receiving the assembled cover and first receptacle, and wherein said cover and said first receptacle may be assembled in said assembled relation of said cover and first receptacle without said second receptacle to form a second liquid sampling device comprising only said cover and said first receptacle and adapted to be placed in a sampling position wherein said basin is disposed to receive a liquid to be sampled, said cover and said second receptacle may be assembled in said assembled relation of said cover and said second receptacle without said first receptacle to form a third liquid sampling device comprising only said cover and said second receptacle and adapted to be placed in a sampling position wherein said basin is disposed to receive a liquid to be sampled, said first receptacle comprises a glass jar having a neck at said upper end of said first receptacle, said first releasably engaging means comprise external threads about said neck of said glass jar, and an internally threaded portion on the lower side of said cover member threadably receiving said jar neck, said second receptacle comprises a canister having an upper end opening, said second releasably engaging means comprises said circumferential portion of said cover member and an upwardly facing shoulder about said upper end opening for seating said circumferential portion of said cover member, the upper side of said cover member is substantially flush with the upper end of said second receptacle in said assembled relation of said cover and second receptacle, said liquid sampling apparatus further comprises a third receptacle having an open upper end and a lower end, and releasably engaging means on said second and third receptacles releasably supporting said first sampling device in assembled relation with said third receptacle wherein (a) said first sampling device is removably positioned within and closes the upper end of said third receptacle, (b) the upper end of said third receptacle extends about and above the upper side of said cover, and (c) the assembled first sampling device and third receptacle form a fourth sampling device adapted to be placed in a sampling position wherein said basin is disposed to receive a liquid to be sampled, said third receptacle comprises a canister having an upper end opening, said third releasably engaging means comprises an outwardly directed flange about said upper end opening of said second receptacle canister, and an internal upwardly facing shoulder about said upper end opening of said third receptacle canister for seating on said flange, and said cover includes at least one of the following: (a) a recess in the upper side of said cover member forming said basin, (b) adjustable valve means for controlling liquid flow rate through said cover passage, and closing said passage in response to filling of the respective sampling device which includes the cover with a certain volume of the liquid being sampled.

13. Liquid sampling apparatus comprising:

a first receptacle having an open upper end and a lower end, a second receptacle having an open upper end and a lower end, a cover including a cover member having upper and lower sides and forming an upwardly opening basin for receiving a liquid to be sampled, and a passage extending through said cover member and opening in said basin and through the lower side of the cover member, first releasably engaging means on said cover member and said first receptacle releasably joining said cover and said first receptacle in assembled relation wherein (a) the upper end of said first receptacle is releasably secured to the lower side of said cover member, (b) said cover member extends laterally beyond the upper end of said first receptacle, whereby the cover member has a circumferential portion about and laterally beyond the upper end of the first receptacle, and (c) said passage opens to the interior of said first receptacle through the upper end of said first receptacle, second releasably engaging means on said cover member and said second receptacle releasably retaining said cover and said second receptacle in assembled relation wherein (a) said cover member extends across and closes the open upper end of the second receptacle, (b) said circumferential portion of said cover member engages said second receptacle about the upper end of said second receptacle, (c) said first receptacle depends from the lower side of said cover member into the interior of said second receptacle through the open upper end of said second receptacle, and (d) said first and second receptacles and said cover form a first liquid sampling device adapted to be placed in a sampling position wherein said basin is disposed to receive a liquid to be sampled and said second receptacle forms a sump removably receiving the assembled cover and first receptacle, and wherein said cover and said first receptacle may be assembled in said assembled relation of said cover and first receptacle without said second receptacle to form a second liquid sampling device comprising only said cover and said first receptacle and adapted to be placed in a sampling position wherein said basin is disposed to receive a liquid to be sampled, said cover and said second receptacle may be assembled in said assembled relation of said cover and said second receptacle without said first receptacle to form a third liquid sampling device comprising only said cover and said second receptacle and adapted to be placed in a sampling position wherein said basin is disposed to receive a liquid to be sampled, said first receptacle comprises a glass jar having a neck at said upper end of said first receptacle, said first releasably engaging means comprise external threads about said neck of said glass jar, and an internally threaded portion on the lower side of said cover member threadably receiving said jar neck, said second receptacle comprises a canister having an upper end opening, said second releasably engaging means comprises said circumferential portion of said cover member and an upwardly facing shoulder about said upper end opening for seating said circumferential portion of said cover member, the upper side of said cover member is substantially flush with the upper end of said second receptacle in said assembled relation of said cover and second receptacle, said upper side of said cover member is recessed to form said basin, said liquid sampling apparatus further comprises a third receptacle having an open upper end and a lower end, and releasably engaging means on said second and third receptacles releasably supporting said first sampling device in assembled relation with said third receptacle wherein (a) said first sampling device is removably positioned within and closes the upper end of said third receptacle, (b) the upper end of said third receptacle extends about and above the upper side of said cover member, and (c) the assembled first sampling device and third receptacle form a fourth sampling device adapted to be placed in a sampling position wherein said basin is disposed to receive a liquid to be sampled, said third receptacle comprises a canister having an upper end opening, said third releasably engaging means comprises an outwardly directed flange about said upper end opening of said second receptacle canister, and an internal upwardly facing shoulder about said upper end opening of said third receptacle canister for seating on said flange, said cover includes valve means for controlling flow through said cover passage comprising a perforate valve cage extending below said cover member and having an upper end secured to said cover member about said cover passage with the interior of the cage opening to said cover passage, a valve seat about said passage, a float valve in said cage movable upwardly into contact with said valve seat to close said passage and downwardly away from said valve seat to open said passage, and adjustable stop means on said cage for adjustably limiting downward opening movement of said float valve away to adjust the maximum flow space between said valve seat and said float valve.

14. A liquid sampling device comprising:

a receptacle having upper and lower ends and containing a sample collection chamber, an upwardly opening basin at the upper end of said receptacle for receiving a liquid to be sampled, and liquid inlet means at the upper end of said receptacle including a passage opening to said chamber and having an upper inlet opening to said basin through which liquid may flow from said basin to said chamber, and wherein said sampling device is adapted to be placed in a sampling position wherein said basin is disposed to receive liquid to be sampled, and said inlet means includes float valve means responsive to the liquid level in said chamber for closing said passage in response to filling of said chamber with a predetermined volume of liquid, and means for adjusting the maximum liquid inflow rate into said chamber through said passage.

15. A liquid sampling device according to claim 14 wherein:

said valve means includes a valve seat about said passage, a float valve member movable toward and into contact with said valve seat to close said passage, and said means for adjusting said maximum inflow rate comprises adjustable stop means for adjustably limiting opening movement of said float valve member away from said valve seat.

16. A liquid sampling device according to claim 14 wherein:

said valve means includes a valve seat about said passage, a float valve member within said chamber movable upwardly into contact with said valve seat by rising liquid level in said chamber to close said passage, and said means for adjusting said maximum inflow rate comprises adjustable stop means for adjustably limiting opening movement of said float valve member away from said valve seat.

17. A liquid sampling device according to claim 16 wherein:

said valve means includes a perforate valve cage extending below said valve seat and containing said float valve member for upward movement of the float valve member in the said valve cage into contact with said valve seat and downward movement of the float valve member in the cage away from said valve seat, and said stop means comprises a stop member mounted in the lower end of said cage for engagement by said float valve member and adjustable toward and away form said valve seat.

18. A liquid sampling device according to claim 16 wherein:

said passage is substantially one inch in diameter and one inch in axial length.

19. A liquid sampling device comprising:

a first receptacle having a lower closed end and an upper open end, a removable liquid sampler within said receptacle and insertable into and removable from the receptacle through the open upper end of the receptacle, releasably engaging means on said receptacle and said sampler releasably supporting said sampler in said receptacle, and wherein said sampler includes a second receptacle having an open upper end at said open upper end of said first receptacle, a closed lower end, a liquid collection chamber within said second receptacle, an upwardly opening basin at the upper end of said second receptacle for receiving a liquid to be sampled, and a passage through which liquid can flow from said basin into said collection chamber, said releasably engaging means releasably supports said sampler in a position wherein said second receptacle is located within said first receptacle and said basin is located at the upper end of said first receptacle, said sampler includes a cover releasably secured to and extending laterally beyond the upper end of said second receptacle, whereby the cover has a circumferential portion about and beyond the upper end of said second receptacle, said cover forms said basin and contains said passage, and said releasably engaging means comprises said circumferential portion of said cover and upwardly facing shoulder means about the upper end of said first receptacle seating said circumferential cover portion.

20. A sampling device according to claim 19 wherein:

said first receptacle comprises a canister having an upper end opening, said shoulder means comprises an annular shoulder about said upper end opening, said second receptacle comprises a glass jar having an upper open externally threaded neck, said cover has upper and lower sides, and an internally threaded portion at the lower side of the corner threadably receiving said threaded neck of said jar to releasably secure said jar to said cover, and said passage opens through said cover threaded portion into said glass jar.

* * * * *